(12) United States Patent
Podack et al.

(10) Patent No.: US 8,475,785 B2
(45) Date of Patent: Jul. 2, 2013

(54) ALLOGENEIC CANCER CELL-BASED IMMUNOTHERAPY

(75) Inventors: Eckhard R. Podack, Coconut Grove, FL (US); Koichi Yamazaki, Sapporo (JP); Nozomi Yamazaki, legal representative, Sapporo (JP); Joseph D. Rosenblatt, Hollywood, FL (US)

(73) Assignee: The University of Miami, Miami, FL (US)

( * ) Notice: Subject to any disclaimer, the term of this patent is extended or adjusted under 35 U.S.C. 154(b) by 242 days.

(21) Appl. No.: 12/921,151

(22) PCT Filed: Mar. 3, 2009

(86) PCT No.: PCT/US2009/001330
§ 371 (c)(1),
(2), (4) Date: Sep. 3, 2010

(87) PCT Pub. No.: WO2009/114085
PCT Pub. Date: Sep. 17, 2009

(65) Prior Publication Data
US 2011/0250229 A1 Oct. 13, 2011

Related U.S. Application Data

(60) Provisional application No. 61/033,425, filed on Mar. 3, 2008.

(51) Int. Cl.
*A61K 39/00* (2006.01)
(52) U.S. Cl.
USPC ...................... 424/93.21; 424/93.7; 424/277.1
(58) Field of Classification Search
None
See application file for complete search history.

(56) References Cited

U.S. PATENT DOCUMENTS

| | | |
|---|---|---|
| 4,690,915 A | 9/1987 | Rosenberg |
| 5,188,964 A | 2/1993 | McGuire |
| 5,217,891 A | 6/1993 | Brake |
| 5,232,833 A | 8/1993 | Sanders |
| 5,348,945 A | 9/1994 | Berberian |
| 5,719,044 A | 2/1998 | Shoseyov |
| 5,747,332 A | 5/1998 | Wallen |
| 5,750,119 A | 5/1998 | Srivastava |
| 5,830,464 A | 11/1998 | Srivastava |
| 5,837,251 A | 11/1998 | Srivastava |
| 5,948,646 A | 9/1999 | Srivastava |
| 5,961,979 A | 10/1999 | Srivastava |
| 5,985,270 A | 11/1999 | Srivastava |
| 5,997,873 A | 12/1999 | Srivastava |
| 6,007,821 A | 12/1999 | Srivastava |
| 6,017,540 A | 1/2000 | Srivastava |
| 6,017,544 A | 1/2000 | Srivastava |
| 6,030,618 A | 2/2000 | Srivastava |
| 6,048,530 A | 4/2000 | Srivastava |
| 6,130,087 A | 10/2000 | Srivastava |
| 6,136,315 A | 10/2000 | Srivastava |
| 6,156,302 A | 12/2000 | Srivastava |
| 6,162,436 A | 12/2000 | Srivastava |
| 6,168,793 B1 | 1/2001 | Srivastava |
| 6,322,790 B1 | 11/2001 | Srivastava |
| 6,328,957 B1 | 12/2001 | Colston |
| 6,331,299 B1 | 12/2001 | Rothman |
| 6,383,493 B1 | 5/2002 | Srivastava |
| 6,383,494 B1 | 5/2002 | Srivastava |
| 6,387,374 B1 | 5/2002 | Srivastava |
| 6,399,070 B1 | 6/2002 | Srivastava |
| 6,403,095 B1 | 6/2002 | Srivastava |
| 6,406,700 B1 | 6/2002 | Srivastava |
| 6,410,026 B1 | 6/2002 | Srivastava |
| 6,410,027 B1 | 6/2002 | Srivastava |
| 6,410,028 B1 | 6/2002 | Srivastava |
| 6,436,404 B1 | 8/2002 | Srivastava |
| 6,447,780 B1 | 9/2002 | Srivastava |
| 6,447,781 B1 | 9/2002 | Srivastava |
| 6,451,316 B1 | 9/2002 | Srivastava |
| 6,455,048 B1 | 9/2002 | Srivastava |
| 6,455,503 B1 | 9/2002 | Srivastava |
| 6,461,615 B1 | 10/2002 | Srivastava |
| 6,468,540 B1 | 10/2002 | Srivastava |
| 6,475,490 B1 | 11/2002 | Srivastava |
| 6,605,464 B1 | 8/2003 | Rothman |
| 6,610,659 B1 | 8/2003 | Pramod |

(Continued)

FOREIGN PATENT DOCUMENTS

| | | |
|---|---|---|
| CA | 2158655 | 9/1994 |
| DE | 19602985 | 7/1997 |

(Continued)

OTHER PUBLICATIONS

Wheeler (Salud p'ublica de M'exico, (Jul.-Aug. 1997) 39 (4) 283-7).*
Ezzell, C.: "Cancer "vaccines": an idea whose time has come?", The Journal of Research, 1995, vol. 7:46-49.
Gaiger, A. et al: "Immunity to WT1 in the animal model and in patients with acute myeloid leukemia," Blood, 2000, vol. 95, No. 4:1480-1489.
Gullo, C. and Teoh, G.: "Heat shock proteins: to present or not, that is the question," Immunology Letters, 2004, vol. 94:1-10.

(Continued)

*Primary Examiner* — Karen Canella
(74) *Attorney, Agent, or Firm* — Stanley A. Kim, Esq.

(57) ABSTRACT

Cell-based immunotherapy (e.g., immunization or vaccination) may be improved by frequent administration to a human subject of allogeneic cancer cells secreting a modified heat shock protein (e.g., gp96), depletion of B cells in the subject, or both. Antigen (e.g., epitope derived from neoantigen or tumor antigen of allogeneic or syngeneic cancer cells) may induce a specific immune response in the subject. For example, the epitope bound in an immunogenic complex with the secreted heat shock protein may be obtained from allogeneic cancer cells coexpressing both secreted gp96 and antigen, or from syngeneic cancer cells of the subject expressing only antigen.

4 Claims, No Drawings

U.S. PATENT DOCUMENTS

| | | | |
|---|---|---|---|
| 6,641,812 B2 | 11/2003 | Rothman | |
| 6,656,679 B2 | 12/2003 | Rothman | |
| 6,663,868 B1 | 12/2003 | Rothman | |
| 6,673,348 B2 | 1/2004 | Rothman | |
| 6,719,974 B1 | 4/2004 | Rothman | |
| 6,761,892 B1 | 7/2004 | Rothman | |
| 6,797,480 B1 | 9/2004 | Srivastava | |
| 7,132,109 B1 | 11/2006 | Srivastava | |
| 7,601,359 B1 | 10/2009 | Srivastava | |
| 2003/0170756 A1* | 9/2003 | Berd | 435/7.23 |
| 2005/0019752 A1 | 1/2005 | Franchini | |
| 2007/0141666 A1 | 6/2007 | Dupraz | |
| 2008/0019972 A1* | 1/2008 | Andrieu | 424/144.1 |
| 2008/0026012 A1 | 1/2008 | Podack | |
| 2008/0089901 A1 | 4/2008 | Hanke | |
| 2009/0162404 A1 | 6/2009 | Podack | |
| 2011/0171211 A1 | 7/2011 | Podack | |
| 2011/0223196 A1 | 9/2011 | Podack | |
| 2011/0287057 A1 | 11/2011 | Podack | |

FOREIGN PATENT DOCUMENTS

| | | | |
|---|---|---|---|
| GB | 2251186 | | 7/1992 |
| WO | 8912455 | | 12/1989 |
| WO | 9002564 | | 3/1990 |
| WO | 9102077 | | 2/1991 |
| WO | 9115572 | | 10/1991 |
| WO | 9201717 | | 2/1992 |
| WO | 9208484 | | 5/1992 |
| WO | 9208488 | | 5/1992 |
| WO | 9314118 | | 7/1993 |
| WO | 9317712 | | 9/1993 |
| WO | 9318146 | | 9/1993 |
| WO | 9318147 | | 9/1993 |
| WO | 9321529 | | 10/1993 |
| WO | 9403208 | | 2/1994 |
| WO | 9403599 | | 2/1994 |
| WO | 9404676 | | 3/1994 |
| WO | 9411513 | | 5/1994 |
| WO | 9504824 | | 2/1995 |
| WO | 9506725 | | 3/1995 |
| WO | 9524923 | | 9/1995 |
| WO | 9601611 | | 1/1996 |
| WO | 9602143 | | 2/1996 |
| WO | 9610411 | | 4/1996 |
| WO | 9610419 | | 4/1996 |
| WO | 9631613 | | 10/1996 |
| WO | 9706685 | | 2/1997 |
| WO | 9706821 | | 2/1997 |
| WO | 9706828 | | 2/1997 |
| WO | 9710000 | | 3/1997 |
| WO | 9710001 | | 3/1997 |
| WO | 9710002 | | 3/1997 |
| WO | 9726910 | | 7/1997 |
| WO | 9735619 | | 10/1997 |
| WO | 9823735 | | 6/1998 |
| WO | 9942121 | | 8/1999 |
| WO | 03005964 | | 1/2003 |
| WO | 2004032865 | | 4/2004 |
| WO | WO2005/003136 | * | 4/2005 |
| WO | WO2005/092373 | * | 10/2005 |
| WO | 2009117116 | | 9/2009 |
| WO | 2010060026 | | 5/2010 |
| WO | 2011146828 | | 11/2011 |

OTHER PUBLICATIONS

Heike, M. et al: Protective cellular immunity against a spontaneous mammary carcinoma from ras Transgenic Mice, Immunobiology, 1994, vol. 190:411-423 (Abstract).

Srivastava, P.K. et al: Identification of a human homologue of the murine tumor rejection antigen GP96, Cancer Res, 1989, vol. 49:1341-1343.

Li, J. et al: "Heat shock protein 70 fused to or complexed with hantavirus nucleocapsid protein significantly enhances specific humoral and cellular immune responses in C57BL/6 mice," Vaccine, 2008, vol. 26:3175-3187.

Lucacs, KV et al: "In vivo gene therapy of malignant tumours with heat shock protein-65 gene," Gene Therapy, 1997, vol. 4:346-350.

Viitanen, Paul V. et al: "Mammalian mitochondrial chaperonin 60 functions as a single toroidal ring", The Journal of Biological Chemistry, 1992, vol. 267, No. 2:695-698.

Nicchitta, C.V.: "Biochemical, cell biological and immunological issues surrounding the endoplasmic reticulum chaperone GRP94/gp96," Current Opinion in Immunology, 1998, vol. 10:103-109.

Oizumi, S. et al: "Molecular and cellular requirements for enhanced antigen cross-presentation to CD8 cytotoxic T lymphocytes," The Journal of Immunology, 2007, vol. 179:2310-2317.

Oizumi, S. et al: "Surmounting tumor-induced immune suppression by frequent vaccination or immunization in the absence of B cells," J. Immunotherapy, 2008, vol. 31:394-401.

Philip, R. et al: "Efficient and sustained gene expression in primary T lymphocytes and primary and cultured tumor cells mediated by adeno-associated virus plasmid DNA complexed to cationic liposomes," Molecular and Cellular Biology, 1994:2411-2418.

Podack, E. et al: "Mucosal HIV immunity generated by gp96-SIV/HIV peptide complexes secreted by allogeneic cell," AIDS Research and Human Retroviruses, vol. 24, No. Suppl. 1, p. 91, XP008143997 (Abstract).

Segal, B.H. et al: "Heat shock proteins as vaccine adjuvants in infections and cancer," Drug Discovery Today, 2006, vol. 11:534-540.

Spitler, L.E.: "Cancer Vaccines: The Interferon Analogy," Cancer Biotherapy, 1995, vol. 10:1-3.

Srivastava, P.K.: "Peptide-binding heat shock proteins in the endoplasmic reticulum: role in immune response to cancer an in antigen presentations," Advances in Cancer Research, 1993 (Abstract).

Strbo, N. et al: "Cell-secreted Gp96-Ig-peptide complexes induce lamina propria and intraepithelial CD8+ cytotoxic T lymphocytes in the intestinal mucosa," Immunology, 2010, vol. 3, No. 2 :182-192.

Strbo, N. et al: "Gp96SIV Ig immunization induces potent polyepitope specific, multifunctional memory responses in rectal and vaginal mucosa," Vaccine, 2011, vol. 29, No. 26:2619-2626.

Strbo, N. et al:"Heat shock fusion protein gp96-Ig mediates strong CD8 CTL Expansion in vivo," American Journal of Reproductive Immunology, 2002, vol. 48:220-225.

Strbo, N. et al: "OAO5-04. Gp96-Ig-SIV vaccines induce predominant immune responses at mucosal sites," Retrovirology, 2009, vol. 6:1.

Strbo, N. and Podack, ER.: "Secreted heat shock protein gp96-Ig: an innovative vaccine approach," American Journal of Reproductive Immunology, 2008, vol. 59:407-416.

Strbo, N. et al: "Secreted gp-96-Ig mediates CD8 and NK cell expansion," FASEB Journal, vol. 16, No. 4, 2002, XP008143902 (Abstract).

Strbo, N. et al: "SIV-gp96-Ig vaccine induces high levels of adaptive mucosal CD8 effector cells in rhesus macaques," Journal of Medical Primatology, 2010, vol. 39, X008143996 (Abstract).

Yamazaki, K. et al: "Induction of tumor immunity by gp96 secreted from engineered tumor cells," 2000, Lung Cancer, vol. 29, No. 1, XP027413932 (Abstract).

Welch, W.J. et al: "Purification of the major mammalian heat shock proteins," The Journal of Biological Chemistry, 1982, vol. 257, No. 24:14949-14959.

Zinn, K. et al: "Regulated expression of an extrachromosomal human β-interferon gene in mouse cells," Proc. Natl. Acad. Sci, 1982, vol. 79:4897-4901.

Zuegel, U. et al: "gp96-peptide vaccination of mice against intracellular bacteria," Infect. Immun., 2001, vol. 69 (6):4164-4167.

Wang, X-Y. et al: "Characterization of heat shock protein 110 and glucose-regulated protein 170 as cancer vaccines and the effect of fever-range hyperthermia on vaccine activity," J Immunol, 2001, vol. 166:490-497.

Young, R.A.: "Stress proteins and immunology," Annu. Rev. Immunol., 1990, vol. 8:401-420.

Podack, ER et al.: "Immunotherapy for lung tumors: M17-01," Journal of Thoracic Oncology, 2007, vol. 2(8), Supplement 4: S197-S198.

Yu, W. et al: "Clinical trials with oncolytic adenovirus in China," Current Cancer Drug Targets, 2007, vol. 7:141-148.

Podack, ER et al: "Allogeneic tumor-cell-based vaccines secreting endoplasmic reticulum chaperone gp96," Expert Opin. Biol. Ther., 2007, vol. 7 (11):1679-1688.

Raez, Luis E. et al.: "Lung cancer immunotherapy," Clinical Medicine & Research, 2005, vol. 3, No. 4:221-228.

Multhoff, Gabriele et al.: Heat Shock Protein 72 on Tumor Cells, The Journal of Immunology, 1997, vol. 158:4341-4350.

Dai, Jie et al.: Cell Surface Expression of Heat Shock Protein gp96 enhances Cross-Presentation of Cellular Antigens and the Generation of tumor-specific T cell memory, Cancer Immunity, Jan. 28, 2003, vol. 3:1-11.

Inoue, Satoshi et al.: Inhibitory Effects of B Cells on Antitumor Immunity, Cancer Res 2006, Aug. 1, 2006, vol. 66:7741-7747.

Zheng, Hong et al.: Cell Surface Targeting of Heat Shock Protein gp96 Induces Dendritic Cell Maturation and Antitumor Immunity, The Journal of Immunology, 2001, vol. 167:6731-6735.

Arnold, D. et al., "Influences of Transporter Associated with Antigen Processing (TAP) on the Repertoire of Peptides Associated with the Endoplasmic Reticulum-resident Stress Protein gp96," J. Exp. Med., 1997, vol. 186, No. 3:461-466.

Ausubel, et al., "Current Protocols in Molecular Biology," 1988, vol. 3, Chapter 13, published by Wiley, John & Sons, Incorporated (Abstract).

Barrios, C. et al., "Heat shock proteins as carrier molecules: in vivo helper effect mediated by *Escherichia coli* GroEL and DnaK proteins requires cross-linking with antigen," Clin Exp Immunol, 1994, vol. 98:229-233.

Barrios, C. et al., "Mycobacterial heat-shock proteins as carrier molecules. II: The use of the 70-kDa mycobacterial heat-shock protein as carrier for conjugated vaccinescan circumvent the need for adjuvants and Bacillus Calmette Guerin priming)," European Journal of Immunology, 1992, vol. 22, Issue 6:1365-1372 (Abstract).

Barrios, C. et al., "Specificity of antibodies induced after immunization of mice with the mycobacterial heat shock proteinof 65 kD," Clin Exp Immunol, 1994, 98:224-228.

Blachere, Nathalie E. et al., "Heat shock protein-peptide complexes, reconstituted in vitro, elicit peptide-specific cytotoxic T lymphocyte response and tumor immunity," J. Exp. Med., 1997, vol. 186, No. 8:1315-1322.

Bowen, MA et al., "Structure and expression of murinje CD30 and its role in cytokine production," The Journal of Immunology, 1996, vol. 156, No. :442-449 (Abstract).

Craig, E A., "Chaperones: Helpers Along the Pathways to Protein Folding," Science, 1993, vol. 260, No. 5:1902-1903 (Abstract).

Flynn, et al., "Peptide-binding specificity of the molecular chaperone BiP," Nature, 1991, vol. 353:726-730 (Abstract).

Flynn, et al., "Peptide binding and release by proteins implicated as catalysts of protein assembly," Science, 1989, vol. 245, No. 4916:385-390 (Abstract).

Gething, MJ: "Protein folding in the cell," Nature, 1992, vol. 355:33-45 (Abstract).

Heike, M. et al: "Heat shock protein-peptide complexes for use in vaccines," Journal of Leukocyte Biology, 1996, vol. 60:153-158.

Jakob, U. et al: "Small Heat Shock Proteins Are Molecular Chaperones," The Journal of Biological Chemistry, 1993, vol. 268, No. 3:1517-1520.

Lakey, E.K. et al: "Identification of a peptide binding protein that plays a role in antigen presentation," Proc. Natl. Aced. Sci, 1987, vol. 84:1659-1663.

Lanzavecchia, A.: "Identifying strategies for immune intervention," Science, 1993, vol. 260, No. 5110:937-944 (Abstract).

Li, Z. and Srivastava, P.K.: Tumor rejection antigen gp96/grp94 is an ATPase: implications for protein folding and antigen presentation, The EMBO Journal, 1993, vol. 12, No. 8:3143-3151.

Lindquist, S. "The heat-shock proteins,", Annu. Rev. Genet., 1988, vol. 22:631-77.

Lukacs, L.V. et al: "Tumor cells transfected with a bacterial heat-shock gene lose tumorigenicity and induce protection against tumors," J. Exp. Med, 1993, vol. 178:343-348.

Lussow, A.R. et al: "Mycobacterial heat-shock proteins as carrier molelcules," Eur J Immunol, 1991, vol. 21:2297-302 (Abstract).

Maki, R.G. et al: "Human homologue of murine tumor rejection antigen gp96: 5'-Regulatory and coding regions and relationship to stress-induced proteins," Proc. Nat. Acad. Sci, 1990, vol. 87:5658-5662.

Maki, R.G. et al: "Mapping of the genes for human endoplasmic reticular heat shock protein gp96/grp94," Somatic Cell and Molecular Genetics, 1993, vol. 19, No. 1:73-81 (Abstract).

McCall, C.A. et al: "Biotherapy: A new dimension in cancer treatment," 1989, Nature Biotechnology 7231-240 (Abstract).

Menoret, A. et al: "Co-segregation of tumor immunogenicity with expression of inducible but not constitutive hsp70 in rat colon carcinomas," The Journal of Immunology, 1995, vol. 155, No. 2:740-747 (Abstract).

Munro, Sean and Pelham, H. R.B.: "A C-terminal signal prevents secretion of luminal ER proteins," Cell, 1987, vol. 48, Issue 5:899-907 (Abstract).

Pidoux, A.L. and Armstrong, J.: "Analysis of the BiP gene and identification of an ER retenton signal in *Schizosaccharomyces pombe*," The EMBO Journal, 1992, vol. 11, No. 4:1583-1591.

Rothman, J.E.: "Polypeptide chain binding proteins: catalysts of protein folding and related processes in cells," Cell, 1989, vol. 59, No. 4:591-601 (Abstract).

Srivastava, P.K., et al: "Heat shock proteins transfer peptides during antigen processing and CTL priming," Immunogenetics, 1994, vol. 39:93-98.

Srivastava, P.K., et al: "Chromosomal assignment of the gene encoding the mouse tumor rejection antigen gp96," Immunogenetics, 1988, vol. 28:205-207.

Srivastava, P.K., et al: "Tumor rejection antigens of chemically induced sarcomas of inbred mice," Proc. Natl. Acad. Sci, 1986, vol. 83: 3407-3411.

Srivastava, P.K. and Das, M.R.: "The serologically unique cell surface antigen of zajdela ascitic hepatoma is also its tumor-associated transplantation antigen," International Journal of Cancer, 1984, vol. 33, Issue 3:417-422 (Abstract).

Srivastava, P.K. and Old, L.J.: "Individually distinct transplantation antigens of chemically induced mouse tumors," Immunology Today, 1988, vol. 9, Issue 3:78-83 (Abstract).

Suto, R. and Srivastava, P.K.: "A mechanism for the specific immunogenicity of heat shock protein-chaperoned peptides," Science, 1995, vol. 269, No. 5230:1585-1588 (Abstract).

Udono, H., et al: "Cellular requirements for tumor-specific immunity elicited by heat shock proteins: tumor rejection antigen gp96 primes CD8+ T cells in vivo," Proc. Natl. Acad. Sci, 1994, vol. 91:3077-3081.

Udono, H. and Srivastava, P.K.: "Heat shock protein 70-associated peptides elicit specific cancer immunity," J. Exp. Med., 1993, vol. 178:1391-1396.

Udono, H. and Srivastava, P.K.: Comparison of tumor-specific immunogenicities of stress-induced proteins gp96, hsp90, and hsp70, The Journal of Immunology, 1994, vol. 152, No. 11:5398-5403 (Abstract).

Ullrich, S.J. et al: "A mouse tumor-specific transplantation antigen is a heat shock-related protein," Biochemistry, 1986, Proc. Natl. Acad. Sci., 1986, vol. 83:3121-3125.

Van Den Eynde, B. et al: "The gene coding for a major tumor rejection antigen of tumor P815 is identical to the normal gene of syngeneic DBA/2 Mice," J. Exp. Med., 1991, vol. 173:1373-1384.

Vanbuskirk, A. et al: "A peptide binding protein having a role in antigen presentation is a member of the HSP70 heat shock family," J. Exp. Med., 1989, vol. 170:1799-1809.

Welch, W.J. and Feramisco, J.R.: "Rapid purification of mammalian 70,000-dalton stress proteins: affinity of the proteins for nucleotides," Mol. Cell. Biol., 1985, vol. 5, No. 6:1229-1237 (Abstract).

Welch, W.J. and Suhan, J.P.: "Morphological study of the mammalian stress response: characterization of changes in cytoplasmic organelles, cytoskeleton, and nucleoli, and appearance of intranuclear actin filaments in rat fibroblasts after heat-shock treatment," The Journal of Cell Biology, 1985, vol. 101, No. 4:1198-1211 (Abstract).

Yamazaki, K. et al: Cutting edge: tumor secreted heat shock-fusion protein elicits CD8 cells for rejection, The Journal of Immunology, 1999, vol. 163:5178-5182.

Janetzki, S. et al: "Immunization of cancer patients with autologous cancer-derived heat shock protein gp96 preparations: a pilot study," Int. J. Cancer, 2000, vol. 88:232-238.

Tamura, Y. et al: "Immunotherapy of tumors with autologous tumor-derived heat shock protein preparations," Science Magazine, 1997, vol. 278:117-120 (Abstrct).

Meerovitch, K. et al: "Proparathyroid hormone-related protein is associated with the chaperone protein BiP and undergoes proteasome-mediated degradation," The Journal of Biological Chemistry, 1998, vol. 273:21025-21030.

Bodey, B. et al: Failure of cancer vaccines: the significant limitations of this approach to immunotherapy,: Anticancer Research, 2000, vol. 20:2665-2676.

Boon, T.: "Toward a genetic analysis of tumor rejection antigens," Avances in Cancer Research, 1992, vol. 58:177-210.

Breloer, M. et al: "Isolation of processed, H-2K-binding ovalbumin-derived peptides associated withthe stress proteins HSP70 and GP96," Eur. J. Immunol., 1998, vol. 28:1018-1021.

Evans, T.R.J. and Kaye, S.B.: "Vaccine therapy for cancer—fact or fiction," 1999, Q.J. Med., vol. 92:299-307.

De Gruijl, T. and Curiel, D.T.: "Cancer vaccine strategies get bigger and better," Nature Medicine, 1999, vol. 5, No. 10:1124-1125.

nonymous, Novel tumor vaccine pg96-Ig fusion protein in advanced (stage IIIB), relapsed or metastatic (stage IV) non-small cell lung cancer (NSCLC) patients who have failed first line chemotherapy, ClinicalTrials.gov archive, Dec. 27, 2007; <<http://clinicaltrials.gov/archive/NCT00503568/2007_12_27>>.

Kovalchin, J. T. et al., "Determinants of efficacy of immunotherapy with tumor-derived heat shock protein gp96.", Cancer Immunity, Apr. 27, 2001, vol. 1:7.

Burton, D.R. et al: "Why do we not have an HIV vaccine and how can we make one?," Nature Medicine, 1998, vol. 4:495-498.

Desrosiers, Ronald C.: "Prospects for an AIDS vaccine", Nature Medicine, Mar. 2004, vol. 10, No. 3:221-223.

Girard, M.P. et al: "A review of vaccine research and development: the human immunodeficiency virus (HIV)," Vaccine, 2006, vol. 24:4062-4081.

Matthews, T.J. et al: "Prospects for development of a vaccine against HTLV-III-related disorders," AIDS Research and Human Retroviruses, 1987, vol. 3:197-206.

Strbo, Natasa, et al.: "HLA A2 restricted HIV specific mucosal and systemic immunity induced with secreted heat shock protein gp96-Ig," The FASER Journal, 2008, vol. 22.

* cited by examiner

ALLOGENEIC CANCER CELL-BASED IMMUNOTHERAPY

CROSS-REFERENCE TO RELATED APPLICATION

This application is the U.S. national phase under 35 U.S.C. 371 of International Application No. PCT/US2009/001330, filed Mar. 3, 2009, which designated the U.S., and claims the benefit of U.S. Provisional Application No. 61/033,425, filed Mar. 3, 2008; the entire contents of each of which are hereby incorporated by reference.

FEDERALLY-SPONSORED RESEARCH OR DEVELOPMENT

The U.S. Government has certain rights in this invention as provided for in NIH contract CA039201 from the Department of Health and Human Services.

BACKGROUND OF THE INVENTION

This invention relates to improving cancer cell-based immunotherapy (e.g., immunization or vaccination) comprised of administration of allogeneic cancer cells secreting a modified heat shock protein to a human subject. It is improved by frequent administration of allogeneic cancer cells to the subject, depletion of B cells in the subject before and/or during the first or at least one administration of allogeneic cancer cells, or both.

WO 99/42121 disclosed a cell-based vaccine, wherein modified heat shock protein encoded by a transfected expression construct is secreted. The vaccine may be effective to treat or prevent cancer or infectious disease. One injection of recombinant cancer cells and two injections of recombinant cancer cells separated by two weeks were described. Autologous cancer cells were preferred. By contrast, the present invention uses allogeneic cancer cells.

WO 2005/030136 disclosed inhibiting a tumor by administering a lung cancer cell genetically modified to express CD80 and HLA. The cancer cell does not secrete a modified heat shock protein.

Cancer is typically treated by surgical resection of the tumor, radiation or drugs to kill cancer cells, or a combination thereof. The immune system can inhibit the multiplication and spread of cancer cells. They may escape immunologic surveillance, however, by being nonimmunogenic (e.g., non-small cell lung cancer), which blocks priming of the immune response to generate an effective response, or being immunogenic (e.g., melanoma) but blocking the effector phase of the immune response. Alternatively, blockade of priming could be due to the tumor secreting immunosuppressive mediators or tolerizing chemokines and/or stimulation of regulatory cells, tolerogenic antigen presenting cells, or myelosuppressor cells. Active immunotherapy by administering allogeneic cancer cells could circumvent blockade, and prime the innate and/or adaptive immune response. The induction and amplification of a tumor-specific CD8$^+$ T-cell response would be especially desirable as evaluated by cytolysis of cancer cells or secretion of interferon gamma stimulated by cancer cells.

Raez et al. (J. Clin. Oncol. 22:2800-2807, 2004) described a phase I trial of an allogeneic cancer cell-based vaccine for non-small cell lung cancer in patients with advanced metastatic disease. Adenocarcinoma cell line AD100 was transfected to express CD80 and HLA-A1 or A2. Patients were immunized intradermally with $5 \times 10^7$ cells once every two weeks. Three immunizations represented one course of treatment. Unless a patient had no response to the initial immunization, up to three courses of treatment for a total of nine immunizations were administered. The promising results obtained using this cell-based vaccine might be improved by increasing the frequency of immunization and depleting B cells before and/or during at least one immunization.

Therefore, it is an objective of the present invention to provide improved immunotherapy (e.g., immunization or vaccination), which comprises administering allogeneic cancer cells secreting a modified heat shock protein to a human subject, by frequent administration, depletion of B cells before and/or during the initial or at least one administration, or both. Other advantages and improvements are described below or would be apparent from the disclosure herein.

SUMMARY OF THE INVENTION

The invention provides an improvement in allogeneic cancer cell-based immunotherapy for immunization and vaccination. The "treatment" may be therapeutic, prophylactic, or merely palliative.

A human subject is treated by administering allogeneic cancer cells that secrete a modified heat shock protein (e.g., gp96). Here, "allogeneic" means that the administered cells and the treated subject differ by one or more major histocompatibility complex (MHC) molecules. Heat shock protein may be modified by removing a domain containing the retention signal for endoplasmic reticulum. Optionally, the domain may be replaced with one or more heavy chain constant region(s) of human or mouse immunoglobulin IgG1 or IgG2 (e.g., Fc domain). The modified heat shock protein is expressed from a nucleic acid within the cancer cell that was transfected by an expression vector or infected by a viral vector. The vector may be based on one or more regulatory signal(s) (e.g., transcription start and stop, slice donor and acceptor, polyadenylation, origin of replication) from bovine papilloma virus (BPV). The vector preferably does not contain the E5, E6 and E7 genes of BPV. Thus, the cancer cells can be considered "recombinant" because of the technology used to produce them.

Antigen (e.g., an epitope derived from neoantigen or tumor antigen of an allogeneic or syngeneic cancer cell) may induce an innate or adaptive immune response in the subject. In particular, induction and amplification of a CD8$^+$ T-cell response is desirable. The CD8$^+$ cell may kill cancer cells or secrete interferon gamma specifically.

Optionally, a cancer cell may be made allogeneic by expressing at least one MHC molecule, which is not expressed by the subject, from a nucleic acid within the cancer cell that was transfected by an expression vector or infected by a viral vector. The modified heat shock protein and HLA molecule may be at least partially encoded by the same vector or different vectors.

A human subject may be immunized several times with allogeneic cancer cells. The interval between two consecutive administrations of the cell-based immunogenic composition is less than two weeks. Another improvement may be B-cell depletion of the subject before and/or during at least one administration of the cell-based immunogenic composition.

Further objectives and advantages aspects of the invention will be apparent to a person skilled in the art from the following description of specific embodiments and the claims, and generalizations thereto.

DESCRIPTION OF SPECIFIC EMBODIMENTS OF THE INVENTION

A subject may be administered an immunogenic composition comprising allogeneic cancer cells, which secrete a modified heat shock protein (e.g., a heat shock protein lacking a native retention sequence for endoplasmic reticulum) at least partially encoded by a transfected expression vector or infected viral vector into the cells. As a nascent polypeptide chain, the modified heat shock protein may have its own or another protein's signal sequence to target the secretory pathway. And opposite an N-terminal signal sequence may be a peptide tag comprising one or more constant regions of human immunoglobulin heavy chain (e.g., IgG1 or IgG2). Optionally, the cancer cells express an allogeneic major histocompatibility complex (MHC) molecule (e.g., at least partially encoded by the same or different vector). They may or may not express CD80 (e.g., at least partially encoded by the same or different vector). More details of the expression of modified heat shock protein, HLA-A, and CD80 in various cancer cell lines are provided in WO 99/42121 and WO 2005/030136, which are incorporated by reference.

A subject may be administered in a range from $1 \times 10^7$ to $10 \times 10^7$ allogeneic cancer cells per dosage. A total number of cells from 1 to $10 \times 10^8$ may be administered to the subject. Allogeneic cancer cells may be administered at least twice daily, daily, every other day, twice weekly, weekly, every other week, or monthly between any two consecutive administrations. At least a total of nine, 18 or 27 dosages of allogeneic cancer cells may be administered. Dosages may be administered at intervals of less than two weeks, one week or less, at least twice weekly, at least every other day, at least daily, or at least twice daily. Treatment may continue for at least six weeks, ten weeks, 15 weeks, 18 weeks, 22 weeks, or 26 weeks (e.g., one to six months). During such periods of treatment, cells may be administered at intervals of less than two weeks, one week or less, at least twice weekly, at least every other day, at least daily, or at least twice daily. They may be injected by at least an intradermal, intravenous, intraperitoneal, or subcutaneous route. Each dosage may be split into aliquots for the separate injections that comprise a single administration. Treatment may be improved by frequent vaccination, B-cell depletion, or both.

Antigen (e.g., an epitope derived from neoantigen or tumor antigen of an allogeneic or syngeneic cancer cell) may induce a specific immune response in the subject. For example, the epitope bound in an immunogenic complex with the secreted heat shock protein may be obtained from allogeneic cancer cells coexpressing both secreted gp96 and antigen, or from syngeneic cancer cells of the subject expressing only antigen. The latter would presumably require that modified heat shock protein be taken up by a cancer cell different from where the gp96 was synthesized, and the complex formed in the cancer cell where the antigen was synthesized. Immunization may not require the subject to have functional $CD4^+$ T cells or lymph nodes. Therefore, after all modifications of gp96, including removal of the ER retention signal, the modified gp96 must still bind epitope in an immunogenic complex. Optional modifications include N-terminal additions or deletions, C-terminal additions, point mutations of 1 to 3 contiguous amino acids, or internal additions or deletions from 1 to 10 amino acids.

The subject may be a human subject. The cancer cells may be obtained from a human subject. The immunogen or vaccine may be administered to the same subject who donated the cancer cells or a different subject. Allogeneic cancer cells may have been obtained from a subject differing in transplantation antigen(s) as compared to the subject receiving the cells. Optionally, a major histocompatibility complex molecule (e.g., one or more MHC class I molecules such as HLA-A1, HLA-A2, HLA-A3, HLA-A27) may be expressed in the cancer cells by transfection of an expression vector or infection of a viral vector. The nucleic acid of the vector needs to encode at least partially the modified heat shock protein or allogeneic MHC molecule because the modification or histotype, respectively, may be introduced into an endogenous gene of the cancer cell by homologous recombination.

B cells may be depleted by techniques known in the art, such as ex vivo apheresis or administering antibody specific for a B-cell receptor (e.g., anti-CD19, anti-CD20, anti-CD22, anti-BLyS), dimerized ligand to crosslink a B-cell receptor (e.g., aptamer dimer), or immunosuppressive drug (e.g., cyclophosphamide or prednisolone) may be used. But in contrast to use of rituximab to treat lymphoma or autoimmune disease, B-cell depletion in association with immunotherapy in accordance with the present invention would spare other parts of the immune system to effect cell-based immunotherapy of cancer. For example, rituximab at a dosage from 100 mg/m$^2$ to 500 mg/m$^2$ (or from 200 mg/m$^2$ to 300 mg/m$^2$ or from 350 mg/m$^2$ to 400 mg/m$^2$) may be administered to a patient at a rate of 50 mg/hour to 400 mg/hour one or more times (e.g., once weekly for two weeks to two months). Rituximab may be supplemented with cyclophosphamide and prednisolone. B cells may be depleted then followed by immunotherapy (e.g., immunization or vaccination). The level of B cells may be monitored during immunotherapy and depletion repeated when above 1%, 5% or 10% of normal (i.e., non-depleted) levels.

Cancer cells of a subject undergoing abnormal proliferation may be a neoplasm or tumor (e.g., carcinoma, sarcoma, leukemia, lymphoma), especially lung cancer. Cancers include those originating from the gastrointestinal (e.g., esophagus, colon, intestine, ileum, rectum, anus, liver, pancreas, stomach), genitourinary (e.g., bladder, kidney, prostate), musculoskeletal, pulmonary (e.g., lung), or reproductive (e.g., cervix, ovary, testicle) organ systems. For example, lung cancer may non-small cell lung cancer (e.g., adenocarcinoma, squamous cell carcinoma, or large cell carcinoma), small cell lung cancer, and carcinoids. The cancer cell may be derived from the subject undergoing treatment or from another individual other than the subject. For the former case, allogenicity may be conferred by expressing an unrelated class I molecule of the major histocompatibility complex from a transfected expression vector or an infected viral vector. The cancer cells may be non-immunogenic or have low immunogenicity so long as they are engineered to secrete the modified heat shock protein. They may be from a carcinoma. An exemplary lung cancer cell is the AD100 adenocarcinoma, which is allogeneic for all subjects except the patient from which the cell line was derived and any rare individuals sharing that patient's MHC haplotype. Its derivation is described in WO 2005/030136. AD100 does not express HLA-A1, HLA-A2, or CD80. Pancreatic carcinoma may be treated with MIA PaCa-2 secreting gp96-Ig from ATCC CRL1420; ovarian carcinoma may be treated with OVCAR-3 secreting gp96-Ig from ICLC HTL97004.

Effectiveness of treatment may be evaluated by reduction in symptoms, delayed progression or regression of disease, or prolongation of survival. Or assay of CD8+ T cell cytolysis of cancer cells or interferon gamma stimulated by them may be measured in vitro. Improvement in active immunotherapy may be used to treat cancer in combination with surgery, radiation therapy, and/or chemotherapy. Boosting may occur by administering the immunogenic complex at least monthly for one to two years.

Immunogenic compositions are comprised of allogeneic cancer cells and a pharmaceutically-acceptable carrier and/or vehicle. For example, the carrier may be alginate or PLGA beads or viral particles, and the vehicle may be water for injection or buffered saline solution. Prior to formulating the composition, the carrier or vehicle may be confirmed free of pathogen and pyrogen. Cells may be irradiated and suspended in buffered saline containing 0.5% human serum albumin. The composition is preferably suitable for systemic or local administration by injection or depot. It is preferred that the composition be tested for the absence of bacterial and viral contamination prior to administration. To avoid possible sources of contamination, it would be preferred to culture the allogeneic cancer cells in serum-free, defined medium. Cells may be stored in the same medium supplemented with 20% dimethyl sulfoxide as cryopreservative.

EXAMPLES

Anti-tumor vaccination is quite effective when administered to naïve, tumor-free mice resulting in protection from tumor growth upon subsequent challenge. Protection generally is long lasting and tumor specific indicating the participation of the adaptive immune response. This picture changes radically when vaccines are used for the therapeutic treatment of already established tumor. The same dose of vaccine that is able to effectively establish protective immunity generally is unable to provide therapeutic benefit. The reason for this lack of effectiveness of therapeutic vaccination is thought to stem from the induction of tumor induced suppressor cells, the generation of regulatory cells, the induction of T cell anergy or tolerance, or a combination thereof. Whatever the precise mechanisms of tumor induced immune suppression, the success of vaccine therapy for cancer therapy will depend on overcoming or neutralizing these tumor induced suppressive effects.

Based on pioneering work from the laboratories of Srivastava and Rammensee who showed that heat shock protein gp96-associated peptides are cross-presented to $CD8^+$ cells by dendritic cells, we have developed a vaccination system suitable for antitumor therapy. Transfecting a gp96-IgG1-Fc fusion protein into tumor cells results in secretion of gp96-Ig in complex with chaperoned tumor peptides. Parenteral administration of gp96-Ig secreting tumors triggers robust antigen-specific CD8+ CTL expansion combined with activation of the innate immune system. Tumor secreted gp96 causes the recruitment of DC and NK cells to the site of gp96 secretion and mediates DC activation via binding to CD91 and TLR2 and TLR4. The endocytic uptake of gp96 and its chaperoned peptides triggers peptide cross presentation via MHC class I and strong, cognate CD8 activation independent of $CD4^+$ cells. In this model system $CD8^+$ CTL expansion can be precisely quantitated within 4 to 5 days of vaccination by use of adoptively transferred TCR transgenic, gfp-marked $CD8^+$ T cells. Using this test system we now show that in our model system tumor induced immune suppression is antigen non-specific and can be overcome by frequent immunization or by the absence of B cells.

Subjects, Cell Lines, and Antibodies

C57BL/6J (B6) mice were purchased from The Jackson Laboratory or Charles River Laboratories. Ig-μ-chain deficient mice having a B6 background (DCBM) were purchased from The Jackson Laboratory.

Gfp (green fluorescent protein) mice were obtained from their producers. Transgenic C57BL/6J OT-I mice (obtained from Dr. M. Bevan) express a TCR (Vα2Vβ5.1.2) specific for $H-2K^b$-restricted chicken ovalbumin-derived peptide 257-264 (SIINFEKL). Gfp mice were crossed with OT-I mice to generate gfp-OT-I mice in the animal facility at the University of Miami in accordance with institutional guidelines.

The progeny mice were screened for the expression of the ova-TCR gene and by fluorescence for gfp. All mice were used at 6-12 week of age.

The EG7 cell line (obtained from M. Bevan) was transfected with the vector pCMG-His containing gp96-Ig. Control cells were transfected with vector alone. Lewis lung carcinoma (LLC) cells were obtained from the American Tissue Culture Collection and were transfected with ovalbumin in pAC-neo-ova or with both the ovalbumin vector and pCMG-His containing gp96-Ig. All cells were cultured in IMDM media (GIBCO) with 10% fetal calf serum (FCS) and gentamycin (GIBCO). To maintain transfected cells, antibiotics for selection (G418 or L-Histidinol, Sigma, St. Louis, Mo.) were added to the culture.

The following antibodies were used for staining: anti-CD16/32 (2.4G2), CyChrome-anti-CD3ε (145-2C11), -anti-CD5 (UCHT2), -anti-CD8a (53-6.7), PE-CD19 (4G7), PE or FITC-anti-NK1.1 (PK136), and PE or FITC-anti-CD11c (HL3) were purchased from BD PharMingen.

Purification and Adoptive Transfer of gfp-OT-I cells and $CD19^+$ B Cells

Single-cell suspensions of splenocytes and lymph node (LN) cells were obtained from gfp-OT-I mice and pooled. They were depleted of red blood cells by ammonium chloride lysis. Gfp-OT-I cells were sorted by positive column selection using anti-CD8α magnetic microbeads and a MACS column (Miltenyi Biotec) according to the manufacturer's instructions. The purity of isolated OT-I cells was more than 95% as determined by flow cytometric analysis. Vα2 and Vβ5.1.2 expression on purified cells was quantified by flow cytometry. For purification of B cells, $CD19^+$ cells were purified with anti-CD19 microbeads (Miltenyi Biotec). To reconstitute B cells in BCDM mice, $10^7$ purified cells were adoptively transferred through tail veins two days before transplantation of tumor cells.

Analysis of In Vivo $CD8^+$ CTL Expansion

To measure $CD8^+$ CTL expansion, mice were adoptively transferred with $10^6$ gfp-OT-I, immunized two days later by intraperitoneal (i.p.) injection of $1-4 \times 10^6$ non-irradiated EG7-gp96-Ig cells. Following immunization, cells were harvested from the peritoneal cavity, mesenteric, para-aortic lymph nodes (dLN), and peripheral blood at timed intervals. Red blood cells were removed from samples by ammonium chloride lysis. One million cells were incubated for 10 min at 4° C. with anti-CD16/32 mAb in PBS containing 0.5% BSA (PBA) to block FcR binding. Cells were then incubated with the indicated antibodies for 30 min. Samples were analyzed on a FACScan (Becton Dickinson) with CELL Quest software (BD Bioscience). The total number of the indicated immune cells per each tissue was calculated from the percentage of targeted cells and total number of cells in each tissue.

Tumor Inoculation and Treatment Protocol

Non-irradiated EG7, LLC or LLC-ova cells were injected subcutaneously (s.c.) in 200 μl PBS into the flanks of mice. Five days after inoculation of LLC-ova cells (day 5), $10^6$ purified gfp-OT-I in a volume of 0.3 ml PBS were injected through tail veins. Two days later, mice were immunized by i.p. injection of $10^6$ non-irradiated LLC-ova-gp96-Ig or EG7-gp96-Ig cells in a volume of 0.5 ml PBS according to the schedule indicated in the graphs. Control mice were treated with PBS, EG7 or LLC-ova. The size of tumors in the flank was measured in two dimensions twice per week for at least 20 days.

Statistical Analysis

Significance was evaluated by t-tests. A calculated value of $p < 0.05$ was considered to indicate statistical significance.

Established Tumors Suppress gp96-mediated CD8-CTL Expansion Independent of TCR Specificity Transfection of heat shock fusion protein gp96-Ig into tumor cells results in secretion of gp96-Ig along with gp96-chaperoned peptides. Gp96-Ig is a modified protein generated by the replacement the endoplasmic reticulum retention signal (KDEL) of gp96 with the Fc portion of IgG1. Injection of mice with gp96-Ig secreting tumor cells results in the induction of tumor specific immunity and memory and protection from subsequent challenge with the same, but non-transfected tumor. Tumor immunity generated by secreted gp96-Ig is specific for gp96-chaperoned peptides including peptides derived from tumor endogenous antigens, such as EL4 specific antigens, and for surrogate antigens such as ovalbumin transfected into EL4 (EG7) or LLC (LLC-ova). The ovalbumin surrogate antigen offers a method to accurately determine $CD8^+$ CTL expansion in vivo via adoptive transfer of ovalbumin specific, OT-I TCR transgenic $CD8^+$ cells.

Established tumors are known to be suppressive for CTL expansion. To measure CTL responses in the presence and absence of established tumors, we used the TCR transgenic OT-I system in which transgenic $CD8^+$ CTL respond to ovalbumin-transfected syngeneic or allogeneic tumors secreting gp96-Ig-ova. As transplantable tumor models we used EG7, derived from the EL4 by ovalbumin transfection, which is classified as immunogenic and highly tumorigenic. In addition we also used the Lewis lung carcinoma (LLC and LLC-ova) which is considered less immunogenic and highly tumorigenic. The division rate of both cell lines is very rapid with a doubling time of 8-12 hours in culture.

After a single i.p. immunization with one million EG7-gp96-Ig-cells, secreting 60-80 ng gp96-Ig per $10^6$ cells in 24 hours, OT-I expand from low, preimmune levels in the $CD8^+$ gate (~0.2%) to high frequencies (15-40%) in tumor-free mice. Administration of irradiated EG7 not secreting gp96-Ig is not able to cause significant OT-I expansion. But subcutaneously established EG7 tumors present at a distant site in the flank significantly inhibits gp96-vaccine induced expansion of OT-I in the peritoneal cavity and systemically in spleen and lymph nodes. EG7 tumors secrete ovalbumin and express $K^b$-ova. It is possible therefore that adoptively transferred OT-I upon recirculation through the tumor bed or tumor draining lymph nodes become anergic due to receiving signals through their $K^b$-ova-specific TCR while not receiving costimulatory signal two. To evaluate this hypothesis, the syngeneic tumors EL4 and LLC, neither expressing ovalbumin, were established subcutaneously at distant sites. Subsequently, OT-I where adoptively transferred intravenously (i.v.) and mice immunized i.p. with EG7-gp96-Ig. Established EL4 and LLC were as effective in suppressing OT-I expansion by secreted gp96-ova as established EG7 indicating that suppression is not dependent on the appropriate TCR antigen, $K^b$-ova, in the tumor. While OT-I expansion in the peritoneal cavity and systemically was suppressed by the presence of LLC and EL4 at distant sites, total cell recruitment into the peritoneal cavity upon EG7-gp96-Ig immunization i.p. was actually increased when compared to tumor-free mice.

As also reported by others, the data indicate that established tumors can induce antigen non-specific suppression of CTL expansion. This induction of suppression correlates with increased cellular recruitment to the vaccine site in the peritoneal cavity. Transfer of vaccine induced peritoneal cells from tumor-bearing to tumor-free mice suppressed OT-I expansion in recipient mice indicating the presence of regulatory or suppressor cells. $CD8^+$ T cells thus are non-reactive due to a cellular suppressor response in tumor-bearing mice independent of antigen.

To overcome antigen non-specific immune suppression, we evaluated whether frequently repeated antigen-specific stimulation of $CD8^+$ CTL by vaccination could counteract the suppressive activity found in tumor-bearing mice.

Rejection of Established Tumors Requires Frequent gp96-Ig Immunizations

While many vaccination strategies, including secreted gp96-Ig, are able to establish protective immunity in mice against tumors and tumor antigens, it is more difficult to reject already established tumors by therapeutic vaccination. Given the observation of antigen non-specific suppression of CD8 expansion, we analyzed how different vaccination schedules affected tumor rejection and/or tumor growth.

We initially analyzed the effect of therapeutic vaccination by beginning vaccination on the same day as tumor transplantation. One million EG7 tumor cells were transplanted subcutaneously in the flank of syngeneic mice. On the same day (day 0), one million gp96-Ig secreting EG7 vaccine cells (EG7-gp96-Ig), secreting gp96-Ig at a rate of 60-80 ng/$10^6$ cells×24 hr) were administered i.p. as vaccine and vaccination repeated on day 3, 7, 10 and 14. Compared to mice not receiving therapy, tumor growth is diminished by four EG7-gp96-Ig vaccinations starting on the same day as tumor transplantation. The therapeutic effect is gp96 and antigen dependent. Irradiated EG7, not secreting gp96-Ig, or LLC-gp96-Ig, not expressing EG7-antigens but secreting gp96-Ig at the same rate as EG7-gp96-Ig, are unable to retard tumor growth when administered i.p. as vaccine at the identical dose and schedule as EG7-gp96-Ig. When vaccination with EG7-gp96-Ig is started two days or later after EG7 inoculation, the therapeutic effect using the same vaccination schedule is substantially diminished. These data demonstrate that even after two days established tumors are more difficult to control by vaccination than tumors that are freshly transplanted.

We next evaluated whether established tumors could be controlled by more frequent vaccination schedules. One million EG7 tumor cells were transplanted subcutaneously in the flank and allowed to become established for three to seven days, allowing at least seven or more tumor cell doublings. During this period vascularization of the tumor nodule occurs which is detectable visually. Mice were then vaccinated daily i.p. with one million EG7-gp96-Ig cells or, in specificity controls, with the same schedule and dose of LLC-gp96-Ig cells, or irradiated EG7 cells, or left unvaccinated. Daily vaccination with EG7-gp96-Ig effectively controlled growth of EG7 that had been established for three days, while daily vaccination with irradiated EG7 or with LLC-gp96-Ig had no effect on growth of established EG7. In further studies we allowed the transplanted EG7 tumors to become established for 5 and 7 days before starting vaccination with, EG7-gp96-Ig. Two vaccinations every day were required to retard tumor growth at this later stage of tumor establishment. The data show that frequent immunization can check tumor growth for a period of 24 days in mice. Further studies will be needed to determine whether continued long term vaccination schedules can completely eradicate tumors.

To validate data obtained with the immunogenic EG7 lymphoma, experiments were repeated with less immunogenic, established LLC. Repeated i.p. immunizations (day 3, 7, 10, 14) with LLC-gp96-Ig beginning on the third day after tumor transplantation resulted in retardation of tumor progression of LLC. Daily immunizations for LLC were not more effective in tumor retardation. The effect of immunization was tumor specific as EG7-gp96-Ig vaccination was unable to control LLC tumor growth. Tumor growth control also could not be achieved by irradiated LLC, but was dependent on gp96-Ig secretion.

These data suggest that frequent DC and NK activation combined with antigen cross presentation by secreted gp96-Ig and its chaperoned peptides, can overcome established tumor induced, antigen non-specific immune suppression.

Gp96-mediated DC and NK Recruitment and CD8 CTL Expansion is Enhanced in B Cell Deficient Mice It has been reported by several groups that Th1 antitumor responses are enhanced in B cell deficient mice (BCDM) when compared to wild-type mice. We therefore studied the role of B cells in gp96-mediated CTL expansion and anti tumor immunity. The peritoneal cavity is populated by CD5-CD19+ B cells and by CD5+CD19+ B1-B cells, the latter producing IgM antibody and not undergoing isotype switching upon activation. Upon i.p. immunization with EG7-gp96-Ig the CD5-CD19+ population increases about five fold by day 4 post immunization, while CD5+ B1B cells increase only moderately. Gp96-mediated OT-I expansion is maximal on day 4 and 5 post immunization. It is preceded by recruitment and activation of DC and NK cells in the peritoneal cavity, the site of vaccination. In B-cell deficient mice, the recruitment of DC and especially NK cells was increased in three separate experiments and the recruited cells remained longer in the peritoneal cavity. The difference did not reach significance but was reproducible. Adoptive transfer of wild-type B cells to BCDM abolished increased recruitment of DC and NK cells. The finding suggests that B cells influence gp96-induced recruitment of innate immune cells and suggest that B cells may also be involved in regulating or suppressing $CD8^+$ CTL expansion.

We therefore evaluated whether expansion of gfp-marked OT-I was increased in BCDM. OT-I expansion after gp96-immunization in BCDM was about twice as strong as that seen in wild-type mice by day 4. Importantly, OT-I persisted at significantly higher frequencies on day 7 and 12 post immunization in the peritoneal cavity and in draining lymph nodes. Adoptive transfer of wild-type B cells to BCDM prior to immunization reduced OT-I expansion to levels at or below those seen in wild-type mice. The suppression of OT-I expansion by the presence of B cells is not mediated by IL-10 production since IL-10 deficient mice exhibit OT-I expansion similar to wild-type mice rather than enhanced expansion as seen in BCDM.

Gp96-Mediated Rejection of Established Tumors is Enhanced in the Absence of B Cells As shown above, growth control of established EG7 in wild-type mice minimally requires daily gp96-immunization. Similarly, LLC progression can be retarded by frequent immunizations. EG7 and EL4 cells are rejected in BCDM and do not establish tumors; however LLC and LLC-ova can be established in BCDM although they grow at a slower rate than in wild-type mice. LLC-ova was established subcutaneously in the flank for 7 days in BCDM and in wild-type mice. OT-I were adoptively transferred i.v. and two days later LLC-ova-gp96-Ig was administered as single dose i.p. and tumor growth monitored. In BCDM a single immunization resulted in complete rejection of established, seven day LLC-ova tumors in three mice and significant tumor shrinking in two. In the absence of treatment LLC-ova continued to grow progressively in BCDM albeit at a slower rate than in wild-type mice. B cell reconstitution of BCDM rendered the effect of vaccination similar to that seen in wild-type mice, namely retardation of progression.

Optimal tumor control of established LLC in BCDM by a single immunization is supported both by sufficiently high numbers of tumor specific CTL precursors (OT-I) and by antigen specific immunization (LLC-ova-gp96-Ig). In BCDM the presence of one million adoptively transferred OT-I without gp96-immunization does not result in tumor rejection in the majority of mice. Likewise gp96-immunization alone without OT-I transfer is less effective than the combination.

Clinical Trial of Allogeneic Cancer Vaccine in Non-small Cell Lung Cancer (NSCLC)

The allogeneic, lung cancer cell line AD100 is transfected with gp96-Ig and HLA-A1. At least 70% of the cells express greater than 60 ng gp96-Ig every 24 hours from one million cells. The recombinant cancer cells are irradiated and then injected intradermally into patients suffering from advanced, relapsed, or metastatic NSCLC (stage IIIB/IV). HLA matching is not required. If no concerns about toxicity arise, patients will be vaccinated with $5 \times 10^7$ allogeneic cancer cells once every week or every two weeks over 17 weeks. Alternatively, a total of $4.5 \times 10^8$ allogeneic cancer cells may be delivered by (a) nine injections over 18 weeks, (b) 18 injections over 18 weeks, or (c) 36 injections over 18 weeks.

DISCUSSION

It is well appreciated that established tumors suppress anti-tumor immunity. Tumor specific T cells become anergic in the presence of established tumors. Anergy to the B cell lymphoma used in that study was antigen specific, MHC restricted and dependent on the presence of MHC matched bone marrow derived antigen presenting cells. In other studies antigen non-specific myeloid-suppressor cells and T regulatory cells have been implicated in suppression of anti tumor immunity. Our studies show that suppression of CTL responses in vivo can be achieved by established tumors through antigen-independent pathways. OT-I expansion in response to gp96-ova vaccination is inhibited by established tumors independent of the expression of ovalbumin by the tumors. This type of suppression may be achieved by T regulatory cells or by other suppressor cells such as myeloid-suppressor cells or M2 macrophages. In accord with this hypothesis, the suppressive activity is transferable to tumor-free mice by the transfer of peritoneal cells elicited in tumor-bearing mice by gp96-vaccination.

While the OT-I response to gp96-ova immunization is strongly inhibited in the presence of established tumors, it is not totally blocked, suggesting that there is balance between immune suppression by the established tumor and CD8-CTL activation through antigen cross presentation by activated DC stimulated by secreted gp96-ova. We have shown previously that in tumor naïve mice gp96-ova results in the recruitment and activation of NK and DC followed by OT-I expansion. Established tumors, while actually enhancing recruitment of cells into the peritoneal cavity by LLC-gp96-Ig vaccination, inhibit OT-I expansion and suggest that in the presence of established tumors many of the recruited cells are likely to be suppressor cells. This hypothesis predicts that frequent immunizations with gp96-ova may overcome the suppressive activity by shifting the balance from suppression to increased immune activation through repeated gp96-mediated DC and NK stimulation, increased antigen cross presentation and CTL priming. Indeed frequent immunizations have significant effects on retardation of tumor progression. In the case of established EG7, daily or twice daily vaccinations were more effective in stopping tumor progression. For LLC, immunization every other or every third day were sufficient and daily immunization were not more effective. These tumor specific differences may be related to the rate by which suppressor cells are generated by the presence of the peripheral tumor. Alternatively, it may depend on the mechanism by which tumors mediate the induction of suppressor cells or the nature of the suppressor cells that have been induced. These questions are currently under study.

By studying the OT-I response to i.p. immunization with tumor secreted gp96-ova we noticed that large numbers of B cells are recruited into the peritoneal cavity. B cells have been reported to be inhibitory for anti tumor immunity prompting the question as to their role in gp96 mediated OT-I expansion. Using B cell deficient mice it became clear immediately that B cells inhibit both NK and DC recruitment and OT-I expansion following gp96-ova immunization. B cell reconstituted BCDM responded like wild-type mice to gp96-ova mediated OT-I expansion, ruling out the possibility that B cell deficiency had modified the responsiveness of BCDM to gp96-ova immunization in a manner unrelated to the absence of B cells. B cell deficiency resulted in enhanced OT-I expansion and in strongly enhanced tumor rejection of seven day established LLC-ova tumors even after only a single gp96-Ig immunization. The data suggest that tumor mediated induction of suppressor cells is greatly diminished in the absence of B cells or that B cells them selves act as suppressor cells. Whether B cells participate in the induction of suppressor cells or whether B cells themselves are immunosuppressive for CTL responses needs further study; IL-10 however does not appear to be involved in B cell mediated suppression of tumor immunity. In ongoing studies we have found that OX40-L deficient B cells show reduced ability to suppress anti tumor immune responses. It remains to be determined how OX40-L expressed on B cells mediates suppression of anti tumor immunity and CTL expansion by gp96.

Our studies provide a model by which antigen-independent immune suppression can be studied and further defined. The role of B cells in particular in this process will be of great interest. In addition, our studies point to ways in which anti-tumor vaccines can be made more effective. Depletion of B cells with antibodies and subsequent frequent vaccination, for instance with tumor secreted gp96-vaccines, may result in more efficient control of tumor growth than that seen with conventional vaccination methods.

Patents, patent applications, books, and other publications cited herein are incorporated by reference in their entirety. In particular, the improvements described herein may be applied to administering the cancer cell vaccines of U.S. patent application Ser. No. 11/878,460, which is incorporated by reference.

In stating a numerical range, it should be understood that all values within the range are also described (e.g., one to ten also includes every integer value between one and ten as well as all intermediate ranges such as two to ten, one to five, and three to eight). The term "about" may refer to the statistical uncertainty associated with a measurement or the variability in a numerical quantity which a person skilled in the art would understand does not affect operation of the invention or its patentability.

All modifications and substitutions that come within the meaning of the claims and the range of their legal equivalents are to be embraced within their scope. A claim reciting "comprising" allows the inclusion of other elements to be within the scope of the claim; the invention is also described by such claims reciting the transitional phrases "consisting essentially of" (i.e., allowing the inclusion of other elements to be within the scope of the claim if they do not materially affect operation of the invention) or "consisting of" (i.e., allowing only the elements listed in the claim other than impurities or inconsequential activities which are ordinarily associated with the invention) instead of reciting the "comprising" term. Any of these three transitions can be used to claim the invention.

It should be understood that an element described in this specification should not be construed as a limitation of the claimed invention unless it is explicitly recited in the claims. Thus, the granted claims are the basis for determining the scope of legal protection instead of a limitation from the specification which is read into the claims. In contradistinction, the prior art is explicitly excluded from the invention to the extent of specific embodiments that would anticipate the claimed invention or destroy novelty.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of individual elements disclosed herein are considered to be aspects of the invention. Similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

We claim:

1. A method of immunizing a subject having cancer, said method comprising the steps of:
    administering to the subject doses of an immunogenic composition comprising allogeneic cancer cells that secrete a modified gp96 heat shock protein, wherein the modified gp96 heat shock protein includes a modification which at least removes a domain of native gp96 that contains a retention signal for endoplasmic reticulum, and
    wherein the subject is administered the doses at least nine times, and
    wherein the doses are administered at intervals of less than two weeks.

2. A method of immunizing a subject having cancer, said method comprising: administering to the subject a weekly dose of an immunogenic composition comprising allogeneic cancer cells that secrete a modified gp96 heat shock protein, wherein the modified gp96 heat shock protein includes a modification which at least removes a domain of native gp96 that contains a retention signal for endoplasmic reticulum, wherein the subject is administered the weekly immunogenic composition over at least nine weeks.

3. A method of immunizing a subject having cancer, said method comprising the steps of:
    administering to the subject doses of an immunogenic composition comprising allogeneic cancer cells that secrete a modified gp96 heat shock protein, wherein the modified gp96 heat shock protein includes a modification which at least removes a domain of native gp96 that contains a retention signal for endoplasmic reticulum, and
    wherein the subject is administered the doses at least eighteen times, and
    wherein the doses are administered at intervals of less than two weeks.

4. A method of immunizing a subject having cancer, said method comprising: administering to the subject twice-weekly doses of an immunogenic composition comprising allogeneic cancer cells that secrete a modified gp96 heat shock protein, wherein the modified gp96 heat shock protein includes a modification which at least removes a domain of native gp96 that contains a retention signal for endoplasmic reticulum, wherein the subject is administered the twice-weekly doses over at least eighteen weeks.

* * * * *